United States Patent [19]

Franovich

[11] Patent Number: 4,753,010
[45] Date of Patent: Jun. 28, 1988

[54] STOMA-WAFER CUTTING APPARATUS

[76] Inventor: Anthony Franovich, 122 Magnolia Dr., Belle Chasse, La. 70037

[21] Appl. No.: 840,068

[22] Filed: Mar. 17, 1986

[51] Int. Cl.$^4$ .............................................. B26B 3/00
[52] U.S. Cl. ........................................ 30/124; 30/316; 83/621; 83/635; 83/686
[58] Field of Search ............... 30/124, 130, 290, 301, 30/315, 316, 359, 363; 83/621, 633, 635, 686

[56] References Cited

U.S. PATENT DOCUMENTS

| 545,613 | 9/1895 | Richardson | 30/363 |
|---|---|---|---|
| 1,476,273 | 12/1923 | Swanson | 30/363 X |
| 1,753,305 | 4/1930 | Spalding | 30/316 |
| 2,145,725 | 1/1939 | Jamieson | 30/316 X |
| 2,708,312 | 5/1955 | Hanser | 30/124 |
| 4,391,042 | 7/1983 | Sunderland | 30/316 |

FOREIGN PATENT DOCUMENTS 332318 10/1903 France .................................. 30/363

*Primary Examiner*—Frank T. Yost
*Assistant Examiner*—Michael D. Folkerts
*Attorney, Agent, or Firm*—Pravel, Gambrell, Hewitt, Kimball & Krieger

[57] ABSTRACT

The apparatus of the present invention addresses the unique problem of punching centrally located holes in stoma-wafers, and comprises a base portion fixed to a surface such as a table or the like, the base portion having a raised annular projection for placement of a stoma-wafer thereupon with the projection fittingly engaging into the hole of the stoma-wafer. The base portion further includes an upper arm member fixed to the base portion and extending to a point directly above the location of the raised projection. The fixed member has a vertically movable plunger element with an annular blade threadably attached to the lower end of it, the annular blade being of a size larger than the raised projection, so that movement of the blade downward would cut a hole in the wafer to the appropriate size of the blade as the stoma-wafer is centrally located on the projection.

3 Claims, 3 Drawing Sheets

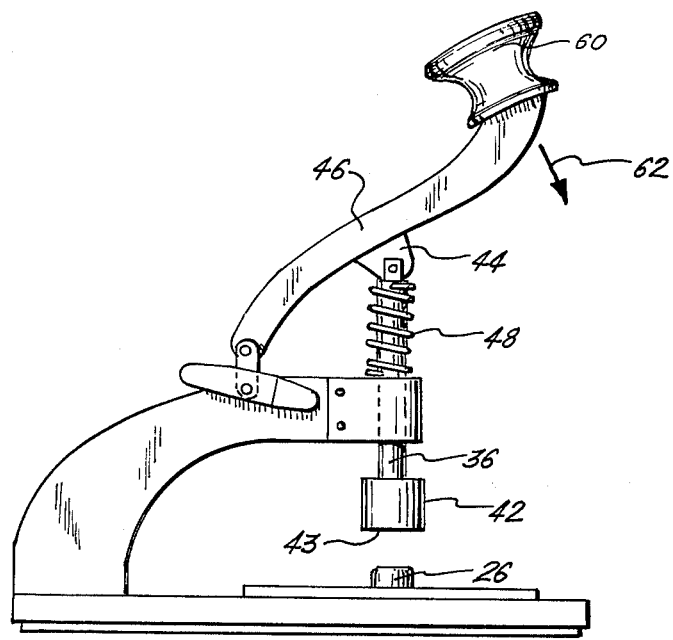
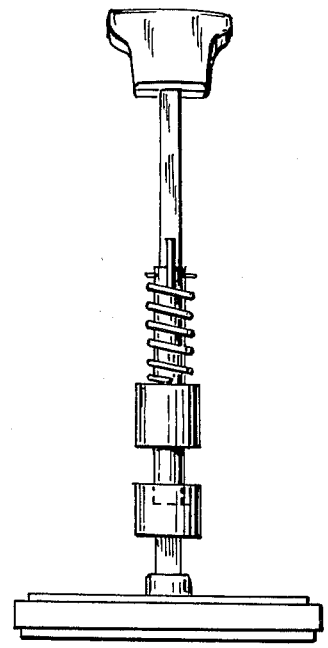
FIG. 2.  FIG. 4.
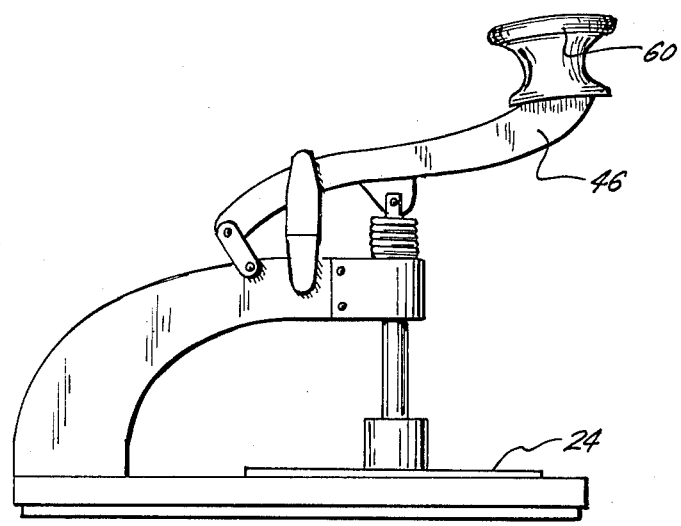
FIG. 3.

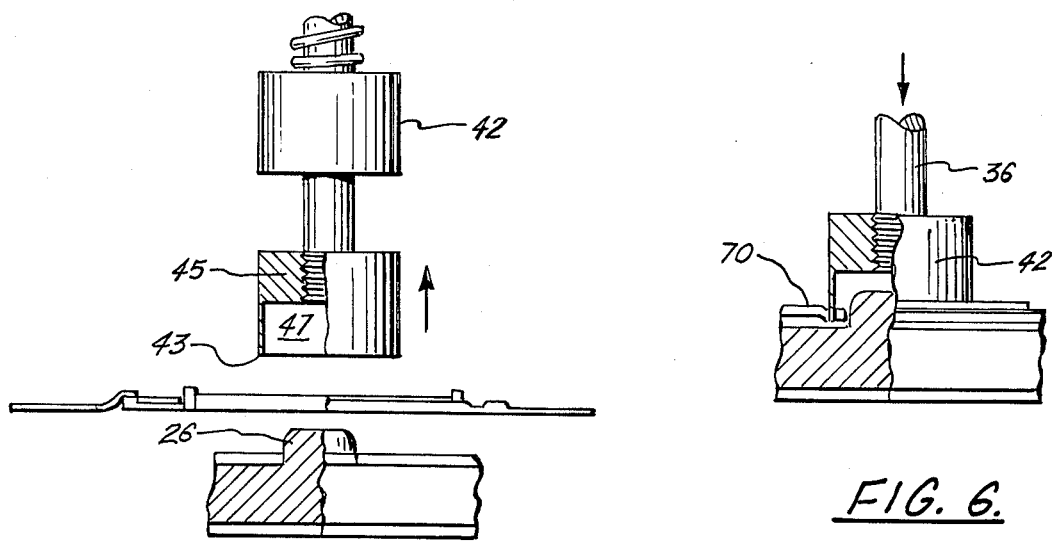
FIG. 5.
FIG. 6.
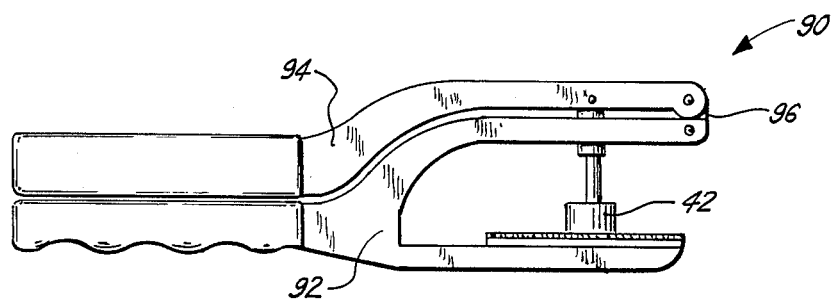
FIG. 7
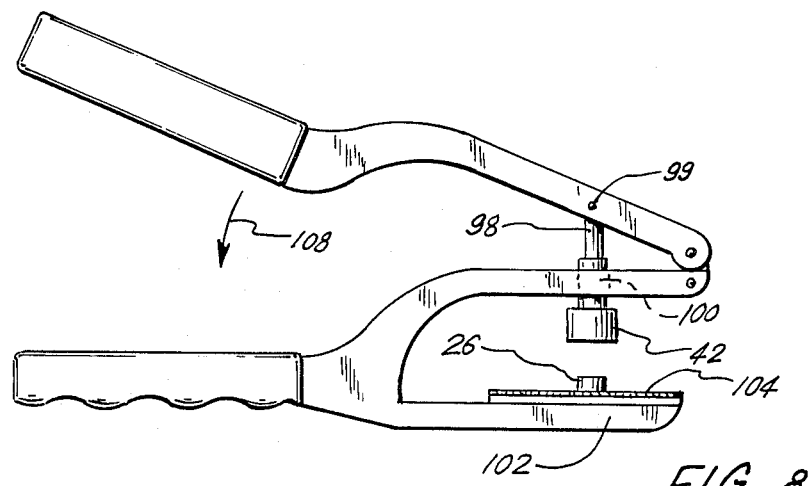
FIG. 8.

STOMA-WAFER CUTTING APPARATUS

BACKGROUND OF THE INVENTION

1. Field Of The Invention:

The present invention relates to an apparatus for cutting an annular hole in an object. More particularly, the apparatus of the present invention relates to a cutting apparatus which is particularly adapted for cutting holes in a stoma-wafer by increasing the diameter of the hole cut over a hole presently contained in the wafer.

2. General Background:

It is often a requirement following surgery on the intestine or the like organ, that an exterior drain hole must be made for allowing drainage of fluids from the body cavity into a container bag or the like attached to the outer person. During the operation of a colostomy or ilostomy, a small part of the intesting is brought to the outside of the body which forms the hole from which the waste products from the body are drained. This opening is called a stoma. This is usually the type of hole that is required following a colostomy, ilostomy or ileocolostomy. The stoma wafer is attached to the skin. The stoma wafer has an adhesive backing which allows it to attach to the skin. The stoma itself passes through the opening. Then a disposable pouch is snapped on to the stoma-wafer. This pouch remains on the individual and contains the waste produced from the body. The pouch can be removed to be emptied or changed as needed. Therefore, the tube actually makes contact with the stoma- wafer rather than the skin making up the exterior of the body orphas.

It is very often, however, that the central hole in the stoma-wafer, which is present when the wafers are obtained, is not of a proper diameter is order to fit the various types of tubes that are adapted to drain the body. Therefore, it is required, usually in all cases, that the central hole in the stoma-wafer be cut to a larger diameter to more perfectly fit the plastic drain tube. In view of the fact that the wafer comprises an adhesive tape backing with a central thickened rubberized area containing the hole in the center, one must use scissors or the like in order to cut through the rubberized central area to enlarge the diameter of the hole presently in the wafer. Of course, this often results in the fact that the edges of the hole cut become jagged, uneven, and no longer centrally located in the center part of the stoma-wafer. This creates problems in attempting to assure that the drain holes is centrally located.

Although there are known in the art, cutters which cut annular holes in templets or the like, the patents found in the art do not address the particular need as addressed by this invention, but these patents for the most part, are as follows:

U.S. Pat. No. 763,225 issued to F. E. Walden entitled "Puncher Or The Like", relates to an apparatus which is a press punch or the like having a frame, a work support arm and a head seperated to permit a plunger mounted on the head to move downward to cut a hole in an object placed in its path. There is also a lever made with the handle opposite the pre-end of the plunger lever to limit the extent of movement of the plunger.

U.S. Pat. No. 794,476 issued to Wilderman entitled "Sheet Metal Punching Device", likewise relates to a device for punching holes through sheet metal having opposite pivoting jaws, gear teeth cut in the jaws and a moveable block interposed between the jaws and engaged by the teeth. A punch held in the block for punching holes in the metal as the jaws are moved.

U.S. Pat. No. 664,846 issued to Espenleub, et al entitled "Punch", also relates to a hand punch for operating on sheet metal so that pressing the handle arms together moves the plunger in the down position to punch the hole in the metal.

U.S. Pat. No. 3,091,855 issued to Hart entitled "Disk Cutter", teaches the use of an apparatus for cutting holes in sheet metal or the like, wherein the sheet of metal is positioned between cooperating cutting components including cooperating disk cutting dies and apperture cutting dies assuring that the metal is cut.

Pat. No. 7239, a German patent, again teaches the use of a hole puncher having a pair of oppositly desposed handles wherein when the handles are pressed, the punch operates to punch a hole through the material.

SUMMARY OF THE PRESENT INVENTION

The apparatus of the present invention addresses the unique problem of punching centrally located holes in stomawafers, and comprises a base portion fixed to a surface such as a table or the like, the base portion having a raised annular projection for placement of a stoma-wafer thereupon with the projection fittingly engaging into the hole of the stoma-wafer. The base portion further includes an upper arm member fixed to the base portion and extending to a point directly above the location of the raised projection. The fixed member has a vertically movable plunger element with an annular blade threadably attached to the lower end of it, the annular blade being of a size larger than the raised projection, so that movement of the blade downward would cut a hole in the wafer to the appropriate size of the blade as the stoma-wafer is centrally located on the projection. The upper portion of the plunger is moved between up and down positions via a movable handle hingedly engaged to a portion of the raised member, and to the upper portion of the plunger, with a spring interposed, so that movement of the handle downward against the bias of the spring moves the blade into the cutting position and following cutting, the handle returns to the up position due to the return of the spring member for an additional cutting.

There is further included a safety member for maintaining the handle in the down position when the cutter is not in use to avoid accidents.

Therefore, it is an object of the present invention to provide a stoma-wafer cutter which cuts a larger centrally located annular hole in the wafer.

It is still a further object of the present invention to provide an apparatus for positioning a stoma-wafer directly centrally located beneath an annular blade, which is movable to a cutting position to achieve a predetermined cut hole directly located in the center of the stoma-wafer.

It is still a further object of the present invention to provide an apparatus having a first position wherein an annular blade is set above a projection for housing a stoma-wafer, and in a second cutting position for cutting a hole in the stoma-wafer, and returning to the first position via the bias of a spring.

It is still a further object of the present invention to provide an additional embodiment of the apparatus wherein the apparatus is held in a person's hand during the cutting operation.

BRIEF DESCRIPTION OF THE DRAWINGS

For a further understanding of the nature and objects of the present invention, reference should be had to the following detailed description, taken in conjunction with the accompanying drawings, in which like part are given like reference numerals and, wherein:

FIG. 2 is a side view of the preferred embodiment of the apparatus of the present invention with the blade in the non-cutting position;

FIG. 3 is a side view of the preferred embodiment apparatus of the present invention with the cutting blade in the down-cutting position;

FIG. 4 is a front view of the preferred embodiment of the apparatus of the present invention;

FIGS. 5 and 6 are partial cutaway views of the annular blade portion of the apparatus of the present invention as seen cutting through a stoma-wafer;

FIGS. 7 and 8 are side views of the additional embodiment of the apparatus of the present invention.

DESCRIPTION OF THE PREFERRED EMBODIMENT

Figure 1:
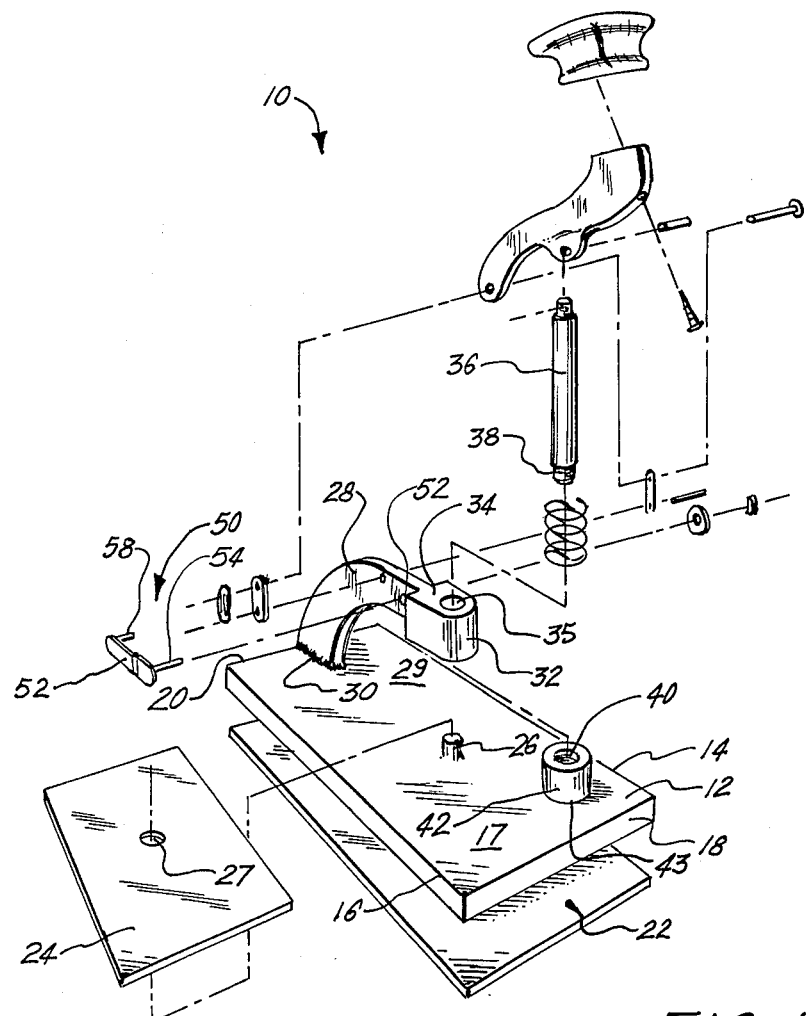
FIG. 1 is an overall exploded view of the preferred embodiment of the apparatus of the present invention.

FIGS. 1-6 illustrate the preferred embodiment of the apparatus of the present invention by the numeral 10. Apparatus 10, shown in exploded view in FIG. 1 comprises a principle base portion 12 which would generally be constructed of metal, and rectangular in shape with side edges 14 and 16 being longer in length in front and rear edges 18 and 20 respectively. Base member 12 would be adhered on its bottom surface to a cushion material 22 such as cork or the like, so that when placement upon a surface such as a table or the like, the apparatus would not tend to scratch the table. The cushion 22 would be adhered to the bottom of base member 12 via gluing or the like. Likewise, base member 12 would have an upper cutter blade absorption portion 24 again, constructed of cork or the like, which would be placed on the upper surface 17 of base member 12, and serve to absorb the cutting blade as will be discussed further.

As seen in the Figure, base member 12 further includes a raised annular projection 26, the use of which will be discussed further, wherein projection 26 would fit through orpheus 27 in absorbing member 24 when member 24 is placed on surface 17 of base member 12, as seen particularly in side view in FIGS. 2 and 3.

Further, base member 12 includes a stationary arm member 28 secured at the rear area 29 of base member 12 with welding or the like at point 30, which stationary arm 28 extending outward over the upper surface 17 of base member 12 to a point 32 directly above projection 26 the function of which will be discussed further. Arm 28 on its furthest most end includes a housing 34 having a port 35 therethrough for housing plunger 36 therethrough, during use of the apparatus. Plunger 36 would have on its lower end threadably attached via threads 38 annular blade 40 which for the most part would include an annular wall portion 42 and a recessed area 43 within the confines of blade 42, as blade 42 is threadably attached onto plunges 36. As seen further in the Figures, plunger 36 is movable within port 35 between up and down positions, with the upper end of plunger 36 adapted to flange 44 adhered to the lower surface of movable handle 46, so that movement of handle 46 between the position seen in FIG. 2 and the position seen in FIG. 3 likewise provides movement to plunger 36 between up and down positions.

There is further included a spring 48 position between the upper face of housing 34 and flange 44, so that when handle 46 is moved to the down position as seen in FIG. 3 it is moved against the bias of spring 48, and upon releasing handle 48, the natural expansion of spring 48 returns handle 46 to the up position as seen in FIG. 2.

For purposes of safety, apparatus 10 further includes a safety means 50 which includes a movable member 52 having a stem projecting through a stem 54 projecting through a port 56 in the body of stationary arm 28, so that member 52 is movable from a position as seen in FIG. 2 to a position as seen in FIG. 3. Member 52 further includes an upper projection 58, which, as seen in FIG. 3 moves to a position blocking any return of handle 46 to the up position and therefore, maintaining it in the position with the annular cutter in the down position. This safety feature therefore would not allow any one to inadvertently injure themselves by pressing down on hand 46 were it in the up position. It is therefore in the "lock" position as seen in FIG. 3.

Having discussed the components of the preferred embodiment in the structure, a discussion will be had of the method of operation. As seen particularly in FIGS. 2-6, particularly in FIG. 2, the apparatus is in position for receiving a stoma-wafer thereupon for cutting. As was discussed earlier, a stoma-wafer is a piece of material approximately 2 inches square, having an annular rubberized thickened area, with a hole in the center. The center hole must be increased in diameter so that the stoma-wafer can accommodate various sizes of plastic drain tubes. In order to accomplish this, the stoma-wafer is placed upon surface 24 with the hole of the stoma-wafer being accommodated by projection 26, which is of the equal diameter to the hole in the stoma-wafer when the stoma-wafer is obtained. Following the positioning of the stoma-wafer thereupon, pressure is put to bear on knob 60 of movable handle 46. As one can see in FIG. 2, the position of handle 46 in the up position has moved annular blade 42 to the up position away from surface 24. Therefore, following the placement of the stoma-wafer onto surface 24, and pressure put to bear on knob 60, handle 46 moves to the down position as seen by Arrows 62 likewise imparting movement to plunger 36 and annular blade 42, so that the annular cutting edge 43 of blade 42 is moved to the position as seen in FIG. 3, i.e., cutting through the stoma-wafer and into the absorption surface 24. Upon removal of pressure from knob 60 of movable handle 46, annular blade moves to the up position as seen in FIG. 2, and the stoma-wafer therefore has the predetermined annular cut in it, as required. For purposes of clarity, FIGS. 5 and 6 illustrate blade 42 as it is in position above stoma-wafer 70, with the cutting edge 43 projecting below the body portion 45 of blade 42, so that there is provided a space 47 within annular blade 42, so that as blade 42 is moved to the position as seen in FIG. 6, it does not make contact with projection 26, so that the stoma-wafer 70 can be cut as seen in FIG. 6.

Therefore, this positioning of stoma-wafer 70 upon annular projection 26 in the downard movement of blade 42, a fixed annular hole can be cut on each stoma-wafer without having to guess whether or not it is centrally located. Likewise, since blade 42 is threadably engaged to plunger 36, various size blades can be utilized depending on the need for the width or the diameter of the hole needed in the stoma-wafer.

FIGS. 7 and 8 illustrate an additional embodiment of the apparatus, which will be designated as 90. Apparatus 90 includes a lower stationary handle portion 92 and an upper movable handle portion 94, the upper and lower handle portions hingedly attached at hinge 96. As seen in the embodiment, handle 94, has attached thereto a plunger 98, which is hingedly engaged at point 99 on its upper end, and has again an annular blade similar to annular blade 42 on its lower end. Likewise, there is provided an orpheus 100 through lower handle member 92, which houses the movement of plunger 98 as it moves upward and downward via the movement of upper handle 99 as seen in FIGS. 7 and 8. Likewise, lower handle means 92 further includes a base portion 102 having a cushion base 104 and again a projecting member 26 as in the preferred embodiment. Therefore, one would simply have to place stoma-wafer 70 onto base member 104 with the hole in stoma-wafer 70 being accommodating projection 26. With the movement of handle member in the down position as indicated by arrow 108, an annular blade 42 moves to the down position as seen in FIG. 7, and likewise cuts stoma-wafer 70 the size hole as required. The additional embodiment would allow one to carry the apparatus in ones bag or purse, should one need one way from ones base.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An apparatus for cutting holes in stoma-wafers, of the type having a pre-cut centrally located hole, the apparatus comprising:
    a. a base portion for placing a stoma-wafer thereupon, the base portion further including a raised member secured thereto, of less or equal diameter to the hole in the stoma-wafer, so that the raised member secured to the base portion protrudes through the hole in the wafer as the wafer is placed upon the base portion;
    b. a support member mounted on the base portion and the end portion of which projects to a position directly above the raised member of the base portion;
    c. annular blade member, supported by the support member, the annular blade member movable between a first up position, and a second down position, so that the blade portion cuttingly engages the stoma-wafer, to cut a larger diametered hole into the wafer, the blade portion being coxially aligned with the raised member when the annular blade is in the down position;
    d. handle means engaged onto the support member, for moving annular blade between up and down positions as the handle means is moved between up and down position; and
    e. spring biasing means positioned between the handle means and the raised member, normally biasing the blade in the up position, but allowing the movement of the blade into the down cutting position against the bias of spring during the cutting operation.

2. The apparatus in claim 1, wherein the annular blade further includes a recessed body portion which defines a means within the blade member for accommodating the annular blade to fit over the raised member in the cutting position.

3. The apparatus in claim 1, further including a means for lockingly engaging the handle in the down position so that the blade is locked in the cutting position.

* * * * *